US007937986B2

(12) United States Patent
Kawasaki et al.

(10) Patent No.: US 7,937,986 B2
(45) Date of Patent: May 10, 2011

(54) SHEET MATERIAL IDENTIFYING APPARATUS, SHEET MATERIAL TREATING APPARATUS AND SHEET MATERIAL IDENTIFYING METHOD

(75) Inventors: Takehiko Kawasaki, Kamakura (JP); Norio Kaneko, Atsugi (JP); Naoaki Maruyama, Honjo (JP)

(73) Assignees: Canon Kabushiki Kaisha, Tokyo (JP); Canon Denshi Kabushiki Kaisha, Saitama-Ken (JP)

( * ) Notice: Subject to any disclaimer, the term of this patent is extended or adjusted under 35 U.S.C. 154(b) by 872 days.

(21) Appl. No.: 10/559,532

(22) PCT Filed: Jun. 10, 2004

(86) PCT No.: PCT/JP2004/008495
§ 371 (c)(1),
(2), (4) Date: Sep. 9, 2008

(87) PCT Pub. No.: WO2004/111616
PCT Pub. Date: Dec. 23, 2004

(65) Prior Publication Data
US 2010/0221030 A1    Sep. 2, 2010

(30) Foreign Application Priority Data

Jun. 12, 2003  (JP) .................................. 2003-168343
Jun. 8, 2004   (JP) .................................. 2004-169853

(51) Int. Cl.
*G01M 7/00* (2006.01)
(52) U.S. Cl. ...................................................... 73/12.01
(58) Field of Classification Search .................. 73/12.01
See application file for complete search history.

(56) References Cited

U.S. PATENT DOCUMENTS

| 5,920,751 | A | 7/1999 | Chow et al. ..................... 399/97 |
| 7,152,861 | B2 | 12/2006 | Kawasaki ...................... 271/262 |
| 2002/0018659 | A1 | 2/2002 | Tomizawa et al. .............. 399/44 |
| 2003/0053089 | A1* | 3/2003 | Nojiri et al. .................... 358/1.9 |
| 2003/0053090 | A1* | 3/2003 | Nojiri et al. .................... 358/1.9 |
| 2003/0063916 | A1 | 4/2003 | Katayanagi et al. ............ 399/44 |
| 2003/0091355 | A1 | 5/2003 | Jeschonek et al. ............. 399/49 |
| 2006/0016996 | A1 | 1/2006 | Kaneko et al. ............. 250/339.1 |
| 2006/0054842 | A1 | 3/2006 | Kawasaki et al. ........ 250/559.04 |
| 2006/0275045 | A1 | 12/2006 | Kawasaki et al. ............... 399/45 |

FOREIGN PATENT DOCUMENTS

| EP | 1 286 156 A2 | 2/2003 |
| EP | 1286156 A2 * | 2/2003 |
| JP | 61-012532 | 1/1986 |
| JP | 2002-139392 | 5/2002 |
| WO | WO 2004/059296 | 7/2004 |
| WO | WO 2004/111616 | 12/2004 |

* cited by examiner

*Primary Examiner* — Hezron Williams
*Assistant Examiner* — Nathaniel Kolb
(74) *Attorney, Agent, or Firm* — Fitzpatrick, Cella, Harper & Scinto

(57) ABSTRACT

To provide a sheet material identifying apparatus for identifying the kind of a sheet material, including an adjusting assembly for dehumidifying or humidifying a predetermined region of the sheet material and adjusting the moisture content of the predetermined region, external force applying means for applying an external force to the predetermined region of the sheet material whose moisture content is adjusted and detecting means for detecting an external force propagated through the sheet while the external force is applied by the external force applying means; wherein an external force is applied to the predetermined region whose moisture content is adjusted through the adjusting assembly by the external force applying means and the kind of a sheet material is identified in accordance with the external force propagated through the sheet detected by the detecting means.

11 Claims, 3 Drawing Sheets

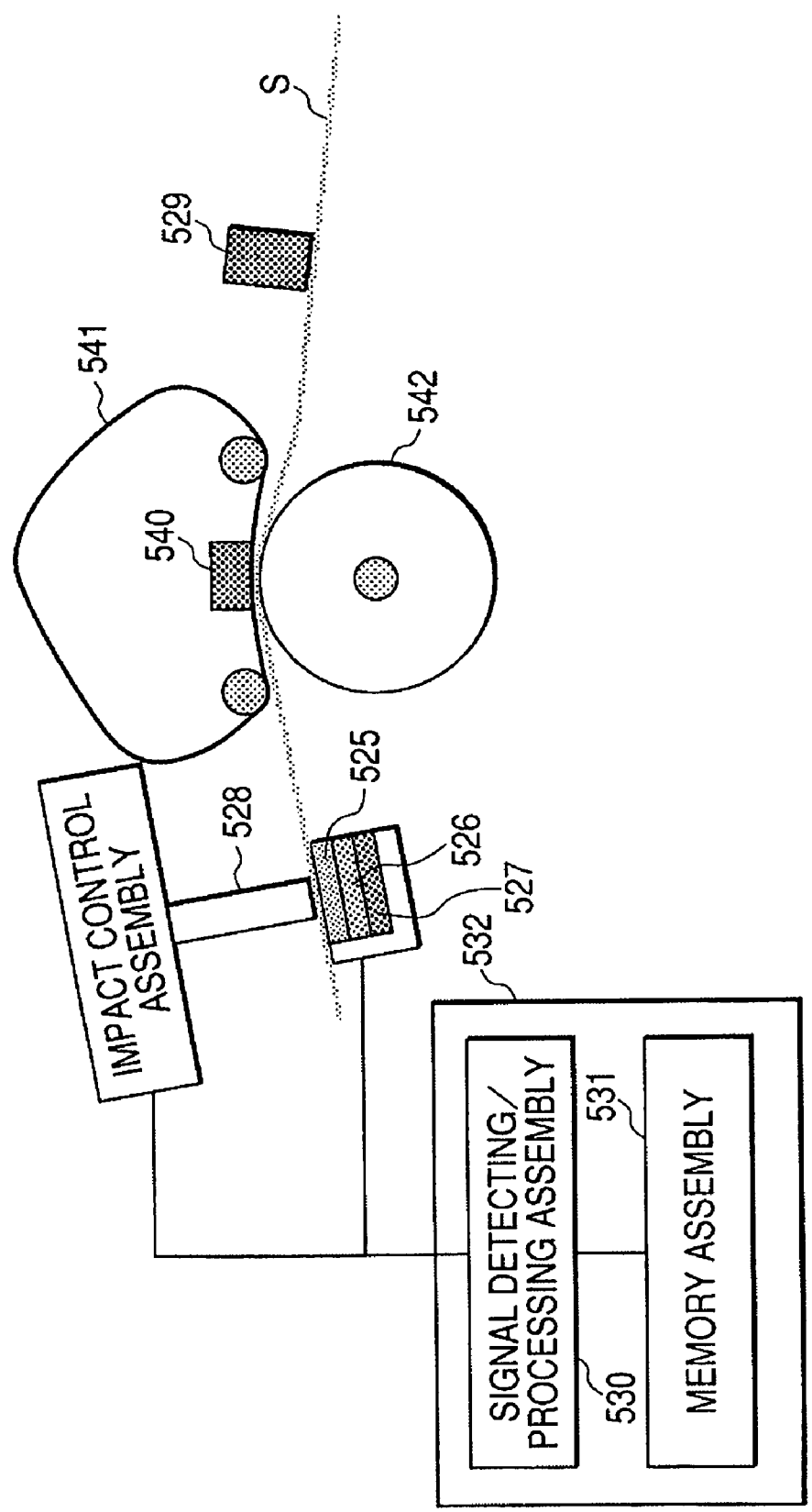

SHEET MATERIAL IDENTIFYING APPARATUS, SHEET MATERIAL TREATING APPARATUS AND SHEET MATERIAL IDENTIFYING METHOD

TECHNICAL FIELD

The present invention relates to a sheet material identifying apparatus, sheet material treating apparatus and sheet material identifying method, particularly to an apparatus for identifying the kind of a sheet material by applying an external force to a sheet material.

BACKGROUND ART

Conventionally, there is a sheet treating apparatus for variously treating a sheet material such as an image forming apparatus for forming an image on a sheet material, image reading apparatus for reading an image on a sheet material or printed matter processing apparatus for classifying and processing printed matters such as bills. Sheet materials to be treated by the above sheet treating apparatus include not only plain paper, glossy paper, coated paper and film-like transparent resin sheet used for an image forming apparatus but also a printed matter such as a bill and various cards.

In this case, there is a sheet treating apparatus which has a sheet material identifying apparatus, identifies the kind of a sheet material by the sheet material identifying apparatus and then performs a treatment corresponding to the sheet material. For example, an image forming apparatus identifies the kind of a sheet material by a sheet material identifying apparatus and then controls a feed speed and a fixing temperature in accordance with the sheet material.

The kind of the sheet material is generally identified by using a difference between forces due to an electrical characteristic or contact friction of the sheet material. However, characteristics of a sheet material are changed due to humidity. Therefore, to identify the kind of the sheet material in accordance with the above method, a method is used in which the humidity in the sheet material identifying apparatus is measured to correct a value relating to the detected electrical characteristic and contact friction in accordance with the measured value (Japanese Patent Application Laid-Open No. 2002-139392).

In the case of the conventional sheet material identifying apparatus and sheet material identifying method, however, a shift may occur between the humidity of the sheet material identifying apparatus and that of a sheet material (that is, moisture content). When the shift is too large, a case is assumed in which the correction performed in accordance with the humidity in the sheet material identifying apparatus is not proper.

Moreover, when correction for the value relating to the electrical characteristic or contact friction thus detected is not properly performed, the sheet material may not be properly treated because the kind of the sheet material is not accurately identified. For example, in the case of an image forming apparatus, a feed speed or fixing temperature corresponding to the kind of a sheet material cannot be properly set and therefore, it may not be possible to form a proper image.

DISCLOSURE OF THE INVENTION

According to an aspect of the present invention, there is provided a sheet material identifying apparatus for identifying the kind of a sheet material comprising: an adjusting assembly for dehumidifying or humidifying a predetermined region of the sheet material and adjusting the moisture content of the predetermined region; an external force applying means for applying an external force to the predetermined region of the sheet material whose moisture content is adjusted; and a detecting means for detecting the external force propagated through the sheet while the external force is applied by the external force applying means; wherein an external force is applied to the predetermined region whose moisture content is adjusted through the adjusting assembly by the external force applying means and the kind of a sheet material is identified in accordance with the external force propagated through the sheet detected by the detecting means. The adjusting assembly is preferably a heating mechanism. The heating mechanism is preferably a fixing device in an electronic photographing apparatus. Alternatively, the heating mechanism is preferably a transfer assembly in a heat transfer printer. The adjusting assembly is preferably a humidifying mechanism. The humidifying mechanism is preferably an ink discharging mechanism (print head) in an ink jet printer. The external force to be applied to the predetermined region by the external force applying means is preferably an impact force or vibration.

The sheet material identifying apparatus preferably further comprises an identifying means for identifying the kind of a sheet material in accordance with the external force detected by the detecting means, wherein the identifying means identifies the kind of the sheet material by comparing the external force with a table previously storing the external forces and the kinds of sheet materials corresponding to the external forces.

Alternatively, the sheet material identifying apparatus preferably further comprises a moisture content detecting means for detecting the moisture content of the sheet material, wherein the moisture content detecting means controls the adjusting assembly so as to adjust the moisture content of the predetermined region of the sheet material in accordance with a moisture content detection result by the moisture content detecting means.

According to another aspect of the present invention, there is provided a sheet treating apparatus comprising the sheet material identifying apparatus, wherein a sheet is treated in accordance with the kind of the sheet material identified by the sheet material identifying apparatus.

According to a further aspect of the present invention, there is provided a sheet material identifying method for identifying the kind of a sheet material, comprising: a moisture content adjusting step of dehumidifying or humidifying a predetermined region of the sheet material to adjust the moisture content of the predetermined region; an external force applying step of applying an external force to the predetermined region of the sheet material whose moisture content is adjusted by an external force applying means; an external force detecting step of detecting the applied external force propagated through the sheet; and an identifying step of identifying the kind of a sheet material in accordance with the detected external force after the moisture content of the predetermined region is adjusted so as to be kept in a predetermined range.

The present invention makes it possible to directly confirm not the humidity in an apparatus but the moisture content of a sheet material whose moisture content is adjusted so as to be kept in a predetermined range by applying an external force to a predetermined region of the sheet material, detecting the external force propagated through the sheet and identifying the sheet material in accordance with the detected external force. Thereby, it is possible to identify the sheet material by also considering the moisture content dependency and accurately identify the sheet material.

BRIEF DESCRIPTION OF THE DRAWINGS

FIG. 5 is a schematic view showing another embodiment of the present invention.

BEST MODE FOR CARRYING OUT THE INVENTION

Embodiments of the present invention will be described below in detail by referring to the accompanying drawings.

Figure 1:
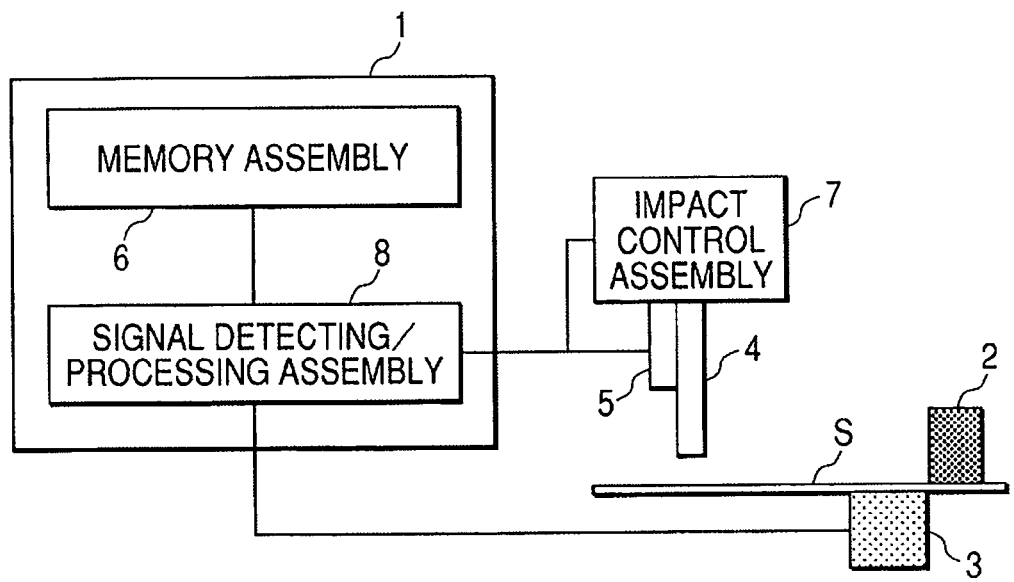
FIG. 1 is an illustration showing a configuration of a sheet material identifying apparatus of an embodiment of the present invention.

FIG. 1 is an illustration for explaining a configuration of a sheet material identifying apparatus of an embodiment of the present invention.

In FIG. 1, reference character S denotes a sheet material, reference numeral 2 denotes a moisture content detecting sensor serving as moisture content detecting means for detecting the moisture content of the sheet material S, 3 denotes a moisture content adjusting assembly serving as an adjusting assembly for adjusting the moisture content of the sheet material S, 4 denotes an impact material serving as external force applying means for applying an impact to the sheet material S as an external force, 5 denotes a detecting sensor serving as detecting means for detecting the external force (impact force) applied by the impact material 4 through the sheet material S and 7 denotes an impact control assembly for controlling an impact applying operation by the impact material 4.

Moreover, reference numeral 1 denotes a control assembly comprising a memory assembly 6 and a signal detecting/processing assembly 8 for detecting a signal sent from the detecting sensor 5 and processing the detected signal sent from the detecting sensor 5. The control assembly 1 constitutes identifying means for comparing a signal processed by the signal detecting/processing assembly 8 with the data stored in a memory assembly 6 and identifying the kind of the sheet material S.

Figure 2:
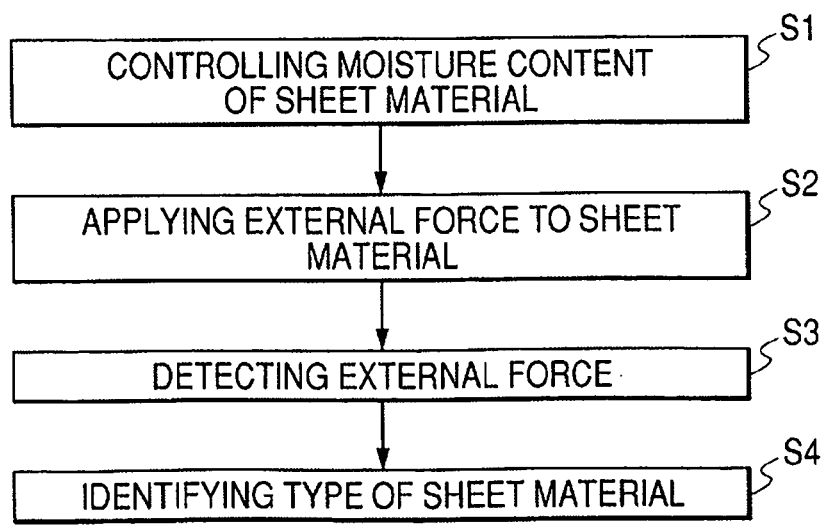
FIG. 2 is a flowchart for explaining the sheet material identifying operation of the sheet material identifying apparatus in FIG. 1.

Then, a sheet material identifying method by the sheet material identifying apparatus having the above constitution will be described below by referring to FIG. 1 and the flowchart shown in FIG. 2.

To identify the sheet material S, the sheet material S is first brought into contact with the moisture content sensor 2 to detect the moisture content of the sheet material S. In this case, when the moisture content is not a desired value, the moisture content of the sheet material S generally shown in % is controlled so that the moisture content becomes a desired value and kept in a predetermined range by using a moisture content adjusting apparatus 3 (S1).

The predetermined range denotes a range between 7.0 and 8.0% which is the moisture content of an average sheet material at a temperature of 23° C. and a humidity of 50%. However, the range is not restricted as long as the sheet material S can be identified without being bedewed.

Moreover, the control assembly 1 dehumidifies or humidifies the sheet material S by controlling the moisture content adjusting apparatus 3 so that the moisture content of the sheet material S is kept in a predetermined range. However, the dehumidifying and humidifying methods are not restricted. To dehumidify the sheet material S, there is a method for evaporating moisture by heating a certain region of the sheet material S or adsorbing moisture by an absorbent.

An adjusting assembly used for the present invention will be described below.

As a preferable mode used for dehumidification, it is possible to use a heater when forming an image on a sheet material. This is a fixing device of toner in electronic photography or a transfer assembly of a heat transfer printer. According to the mode, it is possible to reduce an energy loss because dehumidification is performed by using the heat produced in an image forming step. FIG. 5 shows an example. In FIG. 5, reference numeral 525 denotes an impact receiving material, 526 denotes a detecting sensor for detecting an impact, 527 denotes vibration-proof rubber, 528 denotes an impact material used to apply an impact to the sheet material S, 529 denotes a moisture content detecting sensor, 540 denotes a heater, 541 denotes a fixing film and 542 denotes a pressure roller. The heater 540, fixing film 541 and pressure roller 542 constitute a fixing device of toner in an electronic photographing apparatus. In the case of this mode, the sheet material S is fed from right to left in FIG. 5 and heated by the heater 540 to adjust the moisture content and detect information.

Moreover, as a preferable mode used for humidification, it is possible to use a mechanism for supplying ink to a sheet material when forming an image on the sheet material. This is an ink discharging mechanism (print head) or the like in an ink jet printer. As a moisture source to be supplied to a sheet material in order to humidify the sheet material, ink of a print, a medical agent used for coating of a sheet material and water are properly used.

Furthermore, in a mode for adjusting moisture in the above step of forming an image, it is also allowed to once detect information from a sheet material heated for image formation and the mode is useful for the following.

Both-side printing and multiple printing of the sheet material to be detected

Continuous printing of the same type of sheet materials

Furthermore, in the case of humidification, there is a method for spraying water on a certain region of the sheet material S together with air.

The moisture content adjustment control is not necessary for the whole sheet but it is allowed that the moisture content in a region to which an external force is applied is controlled so that the moisture content is kept in a predetermined range in an external force applying step to be described later. It is naturally allowed to control the whole sheet.

Moreover, as the moisture content detecting sensor 2 for detecting the moisture content of the sheet material S, it is possible to use an electric-resistance hygrometer for measuring an electric resistance which is changed due to a moisture content and detecting the moisture content.

Furthermore, it is also preferable for the moisture content detecting sensor 2 to measure the humidity of the air very close to the sheet material S. In this case, a holding mechanism for setting a humidity sensor very closely to the surface of a sheet material is provided for the humidity sensor. It is preferable to use a quick-response humidity sensor. For example, it is preferable to use a sensor for detecting a change of dielectric characteristics corresponding to an ambient humidity by an object constituted by forming an electrode film on a macromolecular film or a porous thin film made of ceramics or a sensor for detecting a change of heat conductivities corresponding to an ambient humidity by a resistance bulb having a low heat capacity.

Moreover, it is possible for a moisture content detecting sensor to estimate a moisture content by applying a dynamic action to a sheet material and observing the reaction. As an example, it is also allowed to detect that the surface adsorptive power of a sheet material is changed due to a moisture content. As an example of the mechanism, it is also possible to detect a moisture content by performing the contact-removal operations with and from a sheet material while bringing a cantilever probe into a resonant state and detecting the behavior difference between the times of contact and removal as a dynamic phase difference (force curve measurement by interatomic-force microscope. No phase difference appears since the adsorptive power is low at the time of being dry. However, when the quantity of surface adsorbed water increases, a phase difference is increased by the adsorptive power.). Of course, it is allowed to perform the dynamic action by the external force applying means of the present invention. In this case, it is possible to use the external force applying means as a part of moisture content detecting means.

Moreover, as a moisture content detecting sensor, it is allowed to use a moisture content system for measuring absorption by a moisture content by applying infrared radiation or microwaves.

It is allowed to perform the above moisture content detection before or after starting humidification. Of course, it is allowed to detect the moisture content before and after starting humidification. Moreover, it is not necessary to detect the moisture content of the sheet material S by controlling the moisture content to a very high value of 15 to 20% or a low value of 0 to 3%.

Then, after the moisture content adjusting step, an external force is applied to the sheet material S in which moisture content adjustment is controlled (S2). In this case, the external force to be applied to the sheet material S is an impact or vibration. Vibration is applied as an external force by using, for example, a piezoelectric element and thereby, transferring dynamic variation generated at a desired frequency to the sheet material S. Moreover, an impact is applied as an external force by using free fall or a spring and thereby making an impact applying assembly collide with the sheet material S. In the case of this embodiment, an external force is applied to the sheet material S by dropping the impact material 4.

Furthermore, it is preferable to apply an external force to the sheet material S immediately after dehumidifying or humidifying the sheet material S, that is, immediately after the moisture-content adjusting step. Specifically, it is preferable to apply the external force to the sheet material within 10 sec, preferably within 5 sec, more preferably within 1 sec after the moisture content adjusting step.

Then, after the external force applying step, the external force is detected by the detecting sensor 5 through the sheet material S (S3). In this case, the detecting sensor 5 uses a metal-oxide pressure sensor. Moreover, when the pressure sensor is a sensor using a piezoelectric element in which metal oxide is any one of a ferroelectric substance, pyroelectric body and piezoelectric body, it is possible to detect the magnitude of an external force by detecting a voltage generated by the external force transferred through the sheet material or a frequency component of the generated voltage when the external force is applied.

When using free fall other than the above case, repetitive impacts of several times are spontaneously generated due to a one-time impact. Therefore, it is possible to detect a dynamic composition in accordance with the interval time between the repetitive impacts (rebounding time).

In this case, when assuming the first impact due to free fall as the first-time impact, the interval time generates predetermined pulses during the period between the n-th (n is 1 or more) time impact and the m-th (m is an integer equal to or more than 2; and m>n) time impact. Therefore, it is also possible to measure the interval time (rebounding time) in accordance with the number of clock pulses generated by an AND circuit between each pulse and external clock pulse at known frequency.

As shown in FIG. 1, this embodiment detects an external force by directly setting the detecting sensor 5 to the impact material 4. However, it is also allowed to detect an external force by setting the detecting sensor 5 so as to directly or indirectly contact with the sheet material S and applying the external force to the opposite side to the detecting-sensor set side.

Then, after the above external force detecting step, the control assembly 1 processes a value detected by the detecting sensor 5 by the signal detecting/processing assembly 8 and then, identifies the kind of the sheet material S by comparing a data table storing signals output from the detecting sensor 5 through various sheet materials S at a previously-measured predetermined moisture content with an actually-output signal (S4).

In this case, the value detected in the above identifying step reflects all or any one of the informations on the Young's modulus, weighing capacity, density, paper thickness and surface roughness of the sheet material S which is made of a single material or compound material in which a plurality of materials are laminated and thereby, it is possible to identify the sheet material S.

Thus, by applying an external force to a predetermined region of the sheet material S whose moisture content is adjusted, then detecting the external force propagated through a sheet by the detecting sensor 5 and identifying the kind of the sheet material S in accordance with the detected external force, it is possible to identify the sheet material by considering not only the humidity in the sheet material identifying apparatus but also the moisture content dependency of the sheet material and accurately identify the kind of the sheet material.

Then, an embodiment of the sheet material identifying apparatus of this embodiment for identifying a sheet material in accordance with a sheet material identifying method having the above steps will be described below.

Figure 3:
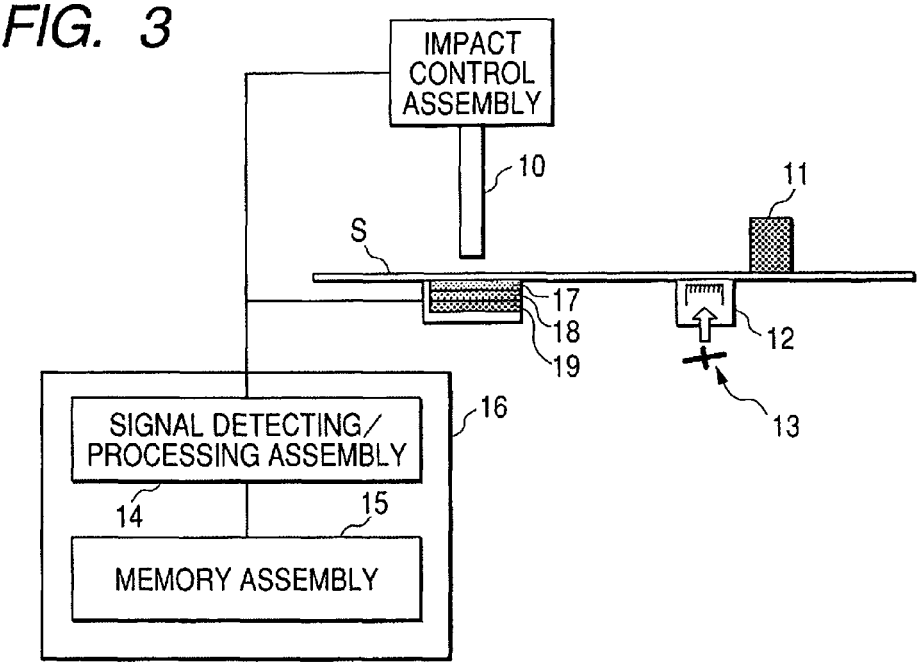
FIG. 3 is an illustration showing a configuration of a sheet material identifying apparatus of a first embodiment of the sheet material identifying apparatus of a the embodiment in FIG. 1.

FIG. 3 is an illustration showing a configuration of the sheet material identifying apparatus of a first embodiment of the sheet material identifying apparatus of this embodiment.

In FIG. 3, reference numeral 10 denotes an impact material made of mild steel and having a weight of 6.64 g used to apply an impact to the sheet material S. In the case of this embodiment, an impact is applied by dropping the impact material 10 onto a sheet material from a height of 2.5 mm. The shape of the front end of the impact material 10 has R 3.5 mm.

Reference numeral 18 denotes a metal-oxide pressure sensor serving as a detecting sensor for detecting an impact. In this case, PZT is used as a metal oxide. Moreover, reference numeral 19 denotes vibration-proof rubber set under the pressure sensor 18 so as not to obtain signals other than an impact applied when the pressure sensor 18 drops the impact material 10 and 17 denotes a brass impact receiving material set to the upside of the pressure sensor 18 for receiving an impact in order to prevent the pressure sensor 18 from being broken due to the impact caused by dropping the impact material 10.

Reference numeral 11 denotes an electric-resistance moisture content detecting sensor and 12 denotes a heating wire used to dehumidify the sheet material S. By supplying the air heated by the heating wire 12 to a certain region at which an impact is applied to the sheet material S so as to detect the kind of the sheet material S by a fan 13, the moisture content of the sheet material S is adjusted. Reference numeral 16 denotes a control assembly having a signal detecting/processing assembly 14 and a memory assembly 15.

Then, the sheet material identifying operation of the sheet material identifying apparatus having the above configuration will be described below. In the case of this embodiment, the identifying operation is described which identifies whether two sheet materials S having been stored in environments different from each other are of the same kind.

First, two sheet materials S of the same kind are prepared which have been stored in environments different from each other to detect the moisture contents of the sheet materials S by the moisture content detecting sensor 11. In this case, moisture contents of the sheet materials S are 7.1% and 9.3%. When an external force is applied to the sheet materials S under the above state, even if the applied external force is detected through the sheet materials S, different values are detected because the sheet materials S have moisture contents different from each other.

Therefore, in the case of this embodiment, because both the sheet materials S are adjusted to a moisture content of 1.0 to 2.0% which is a predetermined moisture content, moisture contents of them are adjusted in a range of 1.0 to 2.0% by using a dehumidifying apparatus constituted by the heating wire 12 and fan 13.

Thereafter, the impact material 10 is dropped onto both the sheet materials S from a height of 2.5 mm. In this case, voltages generated in the pressure sensor 18 due to impact forces propagated through the sheet materials S are 177 mV and 176 mV.

Moreover, the control assembly 16 detects the voltage generated in the pressure sensor 18 by the signal detecting/processing assembly 14 and processes the generated voltage and then compares the processed generated voltage with the data in the memory assembly 15. Thereby, the control assembly 16 can identify that two sheet materials S are of the same kind of sheet materials (Canon color laser copier paper 81.4 g/m$^2$).

Figure 4:
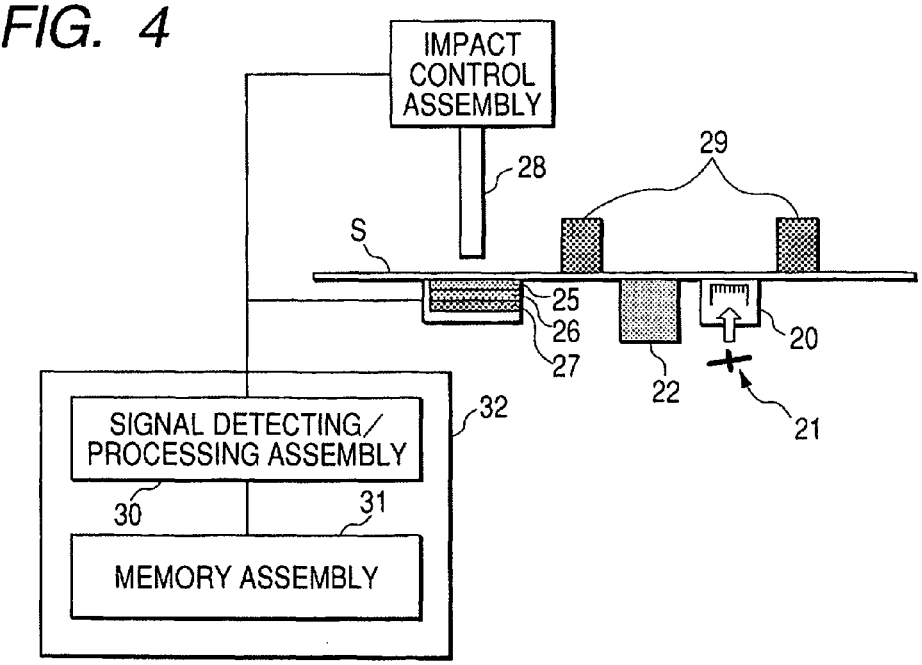
FIG. 4 is an illustration showing a configuration of a sheet material identifying apparatus of a second embodiment of the sheet material identifying apparatus of the embodiment in FIG. 1.

FIG. 4 shows a conceptual view of the configuration of the sheet material identifying apparatus of a second embodiment of this embodiment.

In FIG. 4, reference numeral 28 denotes a mild-steel impact material having a weight of 6.64 g used to apply an impact to the sheet material S. In the case of this embodiment, an impact is applied by dropping the impact material 28 from a height of 2.5 mm. The shape of the front end of the impact material 28 has R 3.5 mm.

Reference numeral 26 denotes a metal-oxide pressure sensor serving as a detecting sensor for detecting an impact. In this case, PZT is used as metal oxide. Moreover, reference numeral 27 denotes vibration-proof rubber set under the pressure sensor 26 so that the pressure sensor 26 does not obtain signals other than an impact applied by dropping the impact material 28 and 25 denotes a brass impact receiving material set to the upside of the pressure sensor 26 for receiving an impact in order to prevent the pressure sensor 26 from being broken due to the impact generated by dropping the impact material 28.

Reference numeral 29 denotes an electric-resistance moisture content detecting sensor and 20 denotes a heating wire used to dehumidify the sheet material S. In the case of this embodiment, the moisture content of the sheet material S is adjusted by moving the sheet material S and supplying the air heated by a heating wire 20 to the whole region of the sheet material S by a fan 21.

Reference numeral 22 denotes a spraying humidifier used for humidification, which adjusts the moisture content of the sheet material S by moving the sheet material S and spraying water vapor on the whole region of the sheet material S. Reference numeral 32 denotes a control assembly having a signal detecting/processing assembly 30 and a memory assembly 31.

Then, the sheet material identifying operation by the sheet material identifying apparatus having the above configuration will be described below. In the case of this embodiment, the identifying operation for identifying two different sheet materials S having been stored in environments different from each other will be described below.

First, two different sheet materials S having been stored in environments different from each other are prepared to detect moisture contents of these sheet materials S by the moisture content detecting sensor 29. As a result, moisture contents of these sheet materials S are 9.4% and 4.5% respectively.

In this case, to previously measure moisture contents of these sheet materials S and adjust the moisture contents to a moisture content of 7.0 to 8.0% which is a moisture content suitable to form an image thereafter, the moisture content of a portion for forming an image of a sheet material S having a high moisture content is adjusted in a range of 7.0 to 8.0% by a dehumidifier constituted by the heating wire 20 and fan 21 and the moisture content of a sheet material S having a low moisture content is adjusted in a range of 7.0 to 8.0% by a humidifier 22.

Moreover, after adjusting the moisture content of the portion for forming an image, it is detected by the moisture content detecting sensor 29 again whether moisture contents of the sheet materials S are kept in a range of 7.0 to 8.0%. When moisture contents are not kept in a range of 7.0 to 8.0% at this point of time, humidification or dehumidification is performed again.

Then, the impact material 28 is dropped onto the two sheet materials S whose moisture contents are kept in a range of 7.0 to 8.0% by humidification or dehumidification from a height of 2.5 mm.

Voltages generated in the pressure sensor 29 due to the impact forces propagated through the sheet materials S are 147 mV and 99 mV. Moreover, the signal detecting/processing assembly 30 processes the generated voltages and then compares the voltage with the data in the memory assembly 31 and thereby, can identify that one of the two sheet materials S is Canon color laser copier paper 81.4 g/m$^2$ (made by CANON INC.) and the other is a thickest sheet for Canon color laser copier paper 209 g/m$^2$ (made by CANON INC.).

After identifying kinds of these two sheet materials S, a not-illustrated image forming apparatus to which the sheet material identifying apparatus is set forms an image in accordance with a setting condition such as a toner fixing temperature for forming an optimum image on these two sheet materials respectively.

It is possible to mount the sheet material identifying apparatus having the above configuration on not only an image forming apparatus and image reading apparatus but also a sheet material treating apparatus such as an automated teller machine, printed matter processing apparatus for classifying and processing printed matters such as bills, automatic article selling machine such as a ticket vending machine or card processing apparatus for processing various cards including a prepaid card.

The invention claimed is:

1. A sheet material identifying apparatus for identifying the kind of a sheet material, comprising:
   an adjusting assembly for dehumidifying or humidifying a predetermined region of the sheet material to adjust the moisture content of the predetermined region to within a predetermined range;
   an external force applying unit for applying an external force to the predetermined region of the sheet material;
   a detecting unit for detecting the external force propagated through the sheet while the external force is applied by the external force applying unit; and
   an identifying unit which uses a detection result of the detection unit for identifying the kind of a sheet material,
   wherein the external force applying unit is provided at a position where the sheet material for which the moisture content has been adjusted is fed and applies the external force to the predetermined region of the sheet material for which the moisture content has been adjusted.

2. The sheet material identifying apparatus according to claim 1,
   wherein
   the adjusting assembly is a heating mechanism.

3. The sheet material identifying apparatus according to claim 2,
   wherein
   the heating mechanism is a fixing device in an electronic photographing apparatus.

4. The sheet material identifying apparatus according to claim 2,
   wherein
   the heating mechanism is a transfer assembly in a heat transfer printer.

5. The sheet material identifying apparatus according to claim 1,
   wherein
   the adjusting assembly is a humidifying mechanism.

6. The sheet material identifying apparatus according to claim 5, wherein
   the humidifying mechanism is an ink discharging mechanism in an ink jet printer.

7. The sheet material identifying apparatus according to claim 1, wherein
   the identifying unit identifies the kind of the sheet material by comparing the external force detected by the detecting unit with a table previously storing the external forces and the kinds of sheet materials corresponding to the external forces.

8. The sheet material identifying apparatus according to claim 1, which further comprises
   a moisture content detecting unit for detecting the moisture content of the sheet material, wherein the moisture content detecting unit controls the adjusting assembly so as to adjust the moisture content of the predetermined region of the sheet material in accordance with a moisture content detection result by the moisture content detecting unit.

9. The sheet material identifying apparatus according to claim 1,
   wherein
   the external force to be applied to the predetermined region by the external force applying means is an impact force or vibration.

10. A sheet material treating apparatus comprising the sheet material identifying apparatus of claim 1, wherein
    sheet treatment parameters are set using information about the kind of the sheet material identified by the sheet material identifying apparatus.

11. A sheet material identifying method for identifying the kind of a sheet material, comprising:
    a moisture content adjusting step of dehumidifying or humidifying a predetermined region of the sheet material to adjust the moisture content of the predetermined region to within a predetermined range;
    an external force applying step of applying an external force to the predetermined region of the sheet material whose moisture content is adjusted by an external force applying means;
    an external force detecting step of detecting the applied external force propagated through the sheet after the external force is applied by the external force applying means; and
    an identifying step which uses a detection result of the detecting step to identify the kind of a sheet material after the moisture content of the predetermined region is controlled so as to be kept in a predetermined range.

* * * * *